United States Patent
Lin et al.

(10) Patent No.: US 7,253,278 B2
(45) Date of Patent: Aug. 7, 2007

(54) PURIFICATION PROCESS FOR MANUFACTURING A HIGH PURE ACARBOSE

(75) Inventors: Chung-Liang Lin, Chiayi (TW); Tung-Li Huang, Chiayi (TW); Jeen-Kuan Chen, Chiayi (TW); Chi-Sheng Wu, Chiayi (TW)

(73) Assignee: Chinese Petroleum Corp, Taipei (TW)

( * ) Notice: Subject to any disclaimer, the term of this patent is extended or adjusted under 35 U.S.C. 154(b) by 501 days.

(21) Appl. No.: 10/790,069

(22) Filed: Mar. 2, 2004

(65) Prior Publication Data

US 2005/0118686 A1 Jun. 2, 2005

(30) Foreign Application Priority Data

Dec. 2, 2003 (TW) .............................. 92133913 A

(51) Int. Cl.
*C07H 1/06* (2006.01)

(52) U.S. Cl. .................... 536/127; 536/18.7; 536/17.2; 536/55.3; 536/124; 536/123.1

(58) Field of Classification Search ................ 536/127, 536/18.7, 17.2, 55.3, 124, 123.1
See application file for complete search history.

(56) References Cited

U.S. PATENT DOCUMENTS 5,989,882 A * 11/1999 Crueger et al. .............. 435/193
6,649,755 B1 * 11/2003 Hong et al. ................. 536/127

FOREIGN PATENT DOCUMENTS

WO WO 99/07720 * 2/1999

* cited by examiner

*Primary Examiner*—Shaojia Anna Jiang
*Assistant Examiner*—Michael C. Henry
(74) *Attorney, Agent, or Firm*—Birch, Stewart, Kolasch & Birch, LLP

(57) ABSTRACT

A process for purifying and preparing highly pure acarbose from acarbose-containing fermentation broth. The acarbose is purified through steps of alcohol precipitation, a strongly acidic cation exchanger chromatography and an immobolized enzyme affinity chromatography. Acarbose is generally applied in treating diabetes.

13 Claims, 5 Drawing Sheets

PURIFICATION PROCESS FOR MANUFACTURING A HIGH PURE ACARBOSE

BACKGROUND OF THE INVENTION

1. Field of the Invention

The present invention relates to a process for manufacturing a highly pure acarbose, and particularly to a process which uses alcohol for precipitation and separation, and a strong cation exchange chromatography and an immobilized enzyme affinity chromatography for manufacturing a highly pure acarbose to treat diabetes.

2. Description of the Related Art

Acarbose,

O-4,6-Dideoxy-[[[1S-(1α,4α,5α,6α)]-4,5,6,-trihydroxy-3-(hydroxymethyl)-2-c yclohexen-1-yl]amino]-α-D-glucopyranosyl-(1→4)-O-α-D-glucopyranosyl-(1→4)-D-glucose, $C_{25}H_{43}NO_{18}$, Mw 645.63, is an oligo-derivative. Acarbose inhibits the activity of α-glucosidase at the edge of the small intestine by invertibility for slowly turning complex carbohydrates and disaccharide into glucose, which can be absorbed by humans, to decrease concentration of triglycerol and insulin in blood and blood sugar.

In the early 1970s, acarbose could improve the ratio of meat and fat, so it was used as an additive in feed for animals such as pigs. Recently, researches have found that acarbose controls the blood sugar of NIDDM and decreases the insulin value after eating, for preventing diabetic carbiovascular complications. However, acarbose cannot directly change insulin resistance. Acarbose only has a few aftereffects, such as abdominal distension, borborygums and diarrhea, which go away after a period of treatment, and hardly affect health. The glucobay of the Bayer was first approved in 1995 by FDA. So far, acarbose is primarily manufactured using *Actinoplanes sp.* or *Streptomyces glaucescens*.

The DOH of Taiwan adjusts the adjusting blood sugar material to be health food. Further, Easterners eats polysaccharide which differs from the fat eaten by Westerners. Therefore, acarbose not only treats diabetes, but can also be used in diet food.

U.S. Pat. No. 4,062,950 sets forth a recover and purification process for manufacturing acarbose, and discloses that acarbose-containing fermentation broth is discolored by anion resins or activated carbons in the acidic condition, and that acarbose are absorbed by activated carbons in the neutral condition and are eluted by ethyl alcohol solution or acetone solution in the acidic condition. The elute passes through the cation exchange chromatography, and acarbose are finally washed by the acid or base solution. The eluted liquid is counteracted and concentrated in the vacuum, and acarbose with 85% purity is precipitated by the organic solvent. The high purity of the acarbose can be manufactured if the exchange chromatography uses celluloses as a matrix. Further, the liquid is concentrated and precipitated by the organic solvent to get a highly pure acarbose. The process is complicated because the process must use activated carbons for absorbing and the exchange chromatography process repeated many times for purification of acarbose.

U.S. Pat. No. 4,174,439 mixes cation and anion exchange resin into acarbose-containing fermentation broth to absorb acarbose and elutes the acarbose by deionized water. The carbose solution is processed twice by a cation and anion exchange resin and is eluted by hydrochloric acid, and is processed with a neutralizing treatment by an anion exchange resin and frozen until dry to acarbose with 52-58% purity.

Further, U.S. Pat. No. 4,666,776 and U.S. Pat. No. 4,767,850 improve U.S. Pat. No. 4,174,439 to use strong cation exchange resin, be washed by hydrochloric acid, be processed by a neutralizing treatment with an anion exchange resin and frozen until dry to get acarbose with 79-82% purity.

The above methods of purifying the acarbose all repeat the anion and cation exchange chromatography to get the acarbose solution and finally use cation exchange chromatography to get a high concentration of acarbose. However, it is difficult to achieve a purity of acarbose sufficient for use as a medical drug.

U.S. Pat. No. 4,904,769 discloses a method in which impure acarbose passes through a weak cation exchange chromatography containing carbonyl, cellulose, and dextran with specific temperature and pH values to get acarbose with a 90% purity. The process is complicated and uses a weak ion exchange chromatography in an expansive process, resulting in high manufacturing costs.

Finally, WO 99/07720 discloses taking an impure acarbose manufactured by U.S. Pat. No. 4,174,439, U.S. Pat. No. 4,666,776 and U.S. Pat. No. 4,767,850, which passes through a strong cation exchange chromatography containing non-aromatic to get highly pure acarbose, and the processes are typically complicated with high manufacturing costs.

SUMMARY OF THE INVENTION

As discussed above, the present invention improves the complicated process and high manufacturing costs of the prior art, and achieves a highly pure acarbose appropriate for use as a medical drug.

The present invention considers processes and material of the above-mentioned prior art, to improve an impure acarbose manufacturing process which applies the solubility between the acarbose and alcohol or methyl alcohol, absorbs the acarbose by strong exchange resin, and eliminates like acarbose by sodium chloride and ammonia solution. The acarbose with a 75-80% purity can be achieved by eluting high concentration ammonia solution, and finally passing through an α-glucosidase column to get up 95% pure acarbose, thereby overcoming the high manufacturing cost costs complicated processes of the prior art.

Further scope of the applicability of the present invention will become apparent from the detailed description given hereinafter. However, it should be understood that the detailed description and specific examples, while indicating preferred embodiments, of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
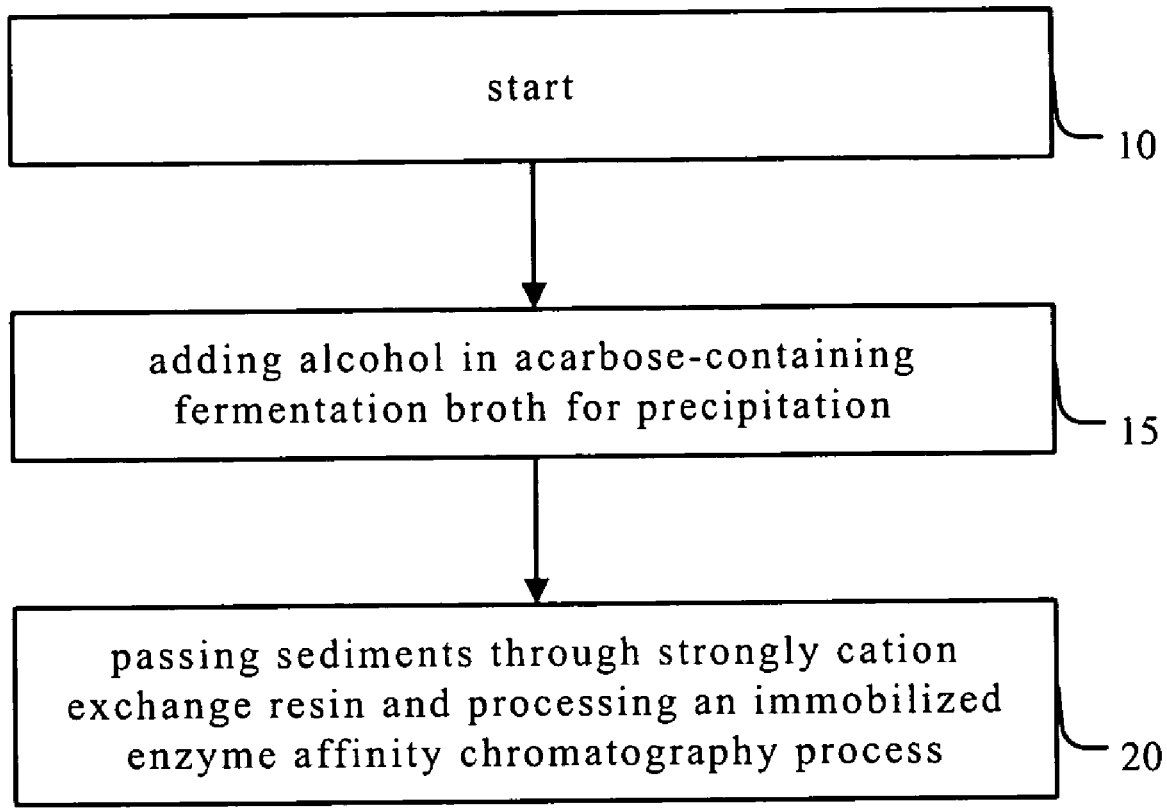
FIG. 1 is a flow chart showing a purification process for manufacturing a highly pure acarbose of the present invention.

Refer to FIG. 1, the present invention discloses a purification process for manufacturing highly pure acarbose comprising the steps of:

Step 10, start;

Step 15, adding alcohol in an acarbose-containing fermentation broth for precipitation;

Step 20, passing sediments through strong cation exchange resin and processing an immobilized enzyme affinity chromatography process.

The present invention discloses a process for purifying acarbose from acarbose-containing fermentation broth to get a highly pure acarbose to treat diabetes. The strong cation exchange chromatography uses styrene divinylbenzene copolymer without methoxymethylmethacrylamide to be a resin matrix, and the enzyme of the immobilized enzyme affinity chromatography uses α-amyloglucosidase(α-glucoamylase).

Further, an upper liquid of the acarbose-containing fermentation broth is made by centrifugal effect or filter and concentrates 1/10 volume by a rotary evaporator concentrating system. Then, adding adequate ethyl alcohol solution or methyl alcohol solution takes an upper liquid by centrifugating, and the upper liquid forms a concentrate. Finally, the concentrate uses ethyl alcohol to get a sediment containing acarbose, and the sediment is dissolved by distilled water to be in a 200 mg/mL concentration. The pH of the dissolved sediment is adjusted to a level of approximately 5-9, to be a mixing liquid.

The process of ion exchange resin uses a strong cation exchange resin, such as AMBERJET 1200 H resin or AMBERJET 1200 Na (Rohm and Hass Company), and is washed by deionized water until the pH value of the upper liquid is larger than 4. Then, the strong cation exchange resin containing 20-200 mg sugar/mL is added into the mixing liquid and blended for 10~30 minutes. A part of the resin is then washed several times with distilled water. The resin is then washed by NaCl to obtain a lot of acarbose-like sugars, and is eluted by an 0.75N ammonia solution. Finally, the resin is dissolved by a 1.5N ammonia solution to get acarbose, which is concentrated and precipitated using ethyl alcohol to get a precipitation in which the purity of acarbose is 75~80%.

Adequate distilled water is added to the impure acarbose powders to adjust the pH value to between five and nine, which is then passed through a column containing AMBERJECT 4400 OH resin and α-amyloglucosidase. Firstly, the column is washed with distilled water having one to four times the volume as column and a temperature of 55~75° C. Then, the acarbose concentrates are collected, and ethyl alcohol is used to obtain a sediment. The sediment is then cooled and dried to increase the purity of the acarbose up to 95%.

EXAMPLE 1

Figure 2:
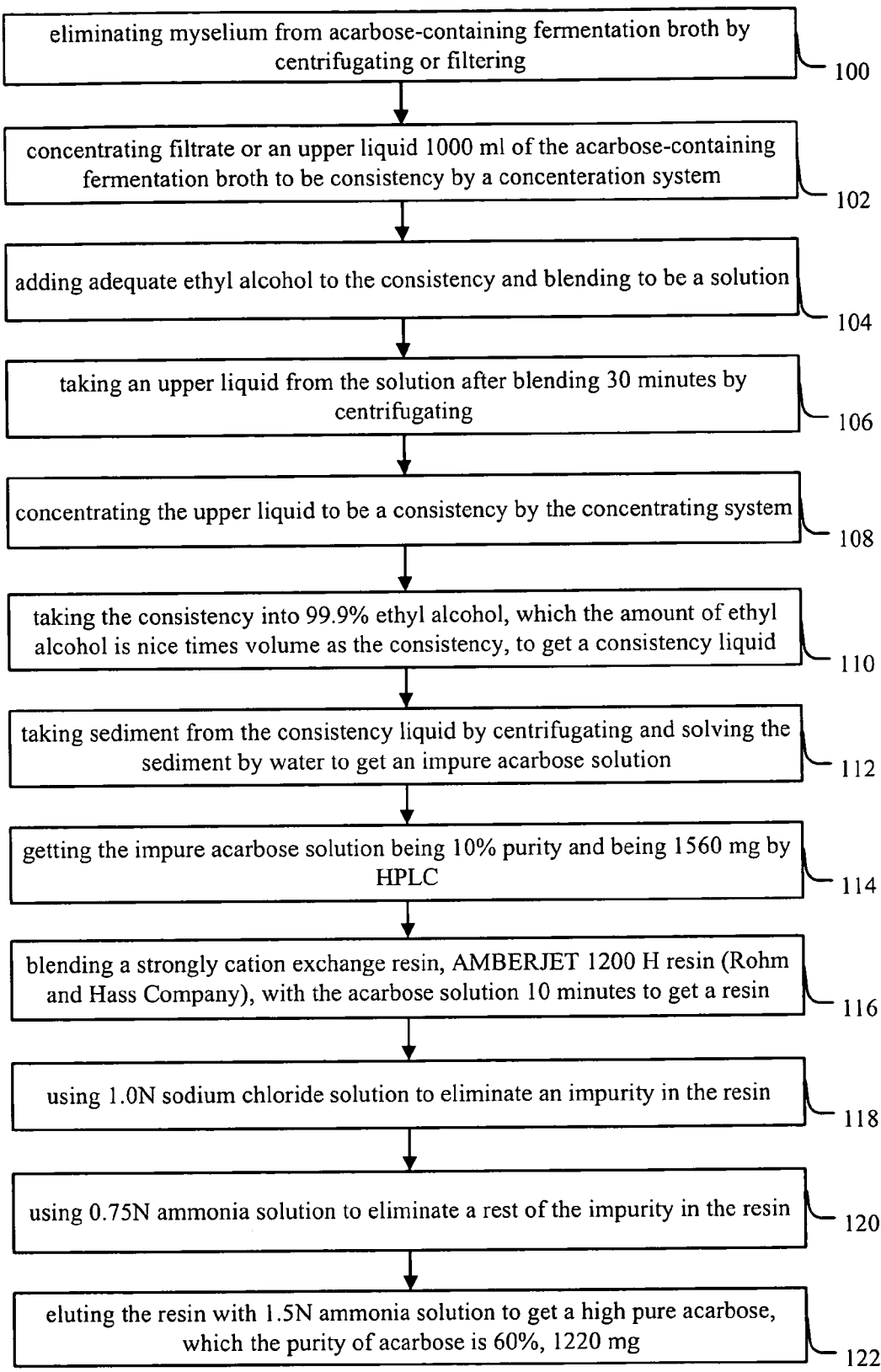
FIG. 2 is flow chart showing a purification process for manufacturing a highly pure acarbose of Example 1 of the present invention.

Referring to FIG. 2, the present invention comprises the following steps:

Step 100: mycelium is eliminated from acarbose-containing fermentation broth by centrifugation or filtration;

Step 102: filtrate or an upper liquid (1000 ml) of the centrifuged acarbose-containing fermentation broth are concentrated by a concentrating system;

Step 104: adequate ethyl alcohol is added to the concentrate and blended into a solution;

Step 106: an upper liquid is taken from the solution by centrifugation after blending for 30 minutes;

Step 108: the upper liquid of the centrifuged solution is further concentrated by the concentrating system;

Step 110: the concentrate is taken into a 99.9% ethyl alcohol solution, wherein the amount of ethyl alcohol is equal to nine times the volume of the concentrate, to obtain a consistency liquid;

Step 112: sediment is removed from the consistency liquid by centrifugation and the sediment is dissolved by water to obtain an impure acarbose solution;

Step 114: using High Performance Liquid Chromatography (HPLC) to obtain an impure acarbose solution with 10%, 1560 mg purity;

Step 116: blending a strong cation exchange resin, such as AMBERJET 1200 H resin (Rohm and Hass Company), with the acarbose solution for 10 minutes, to obtain a resin;

Step 118: using a 1.0N sodium chloride solution to eliminate an impurity in the resin;

Step 120: using a 0.75N ammonia solution to eliminate further impurities in the resin; and Step 122: eluting the resin with a 1.5N ammonia solution to obtain highly pure acarbose, in which the purity of the acarbose is 60%, 1220 mg.

EXAMPLE 2

Figure 3:
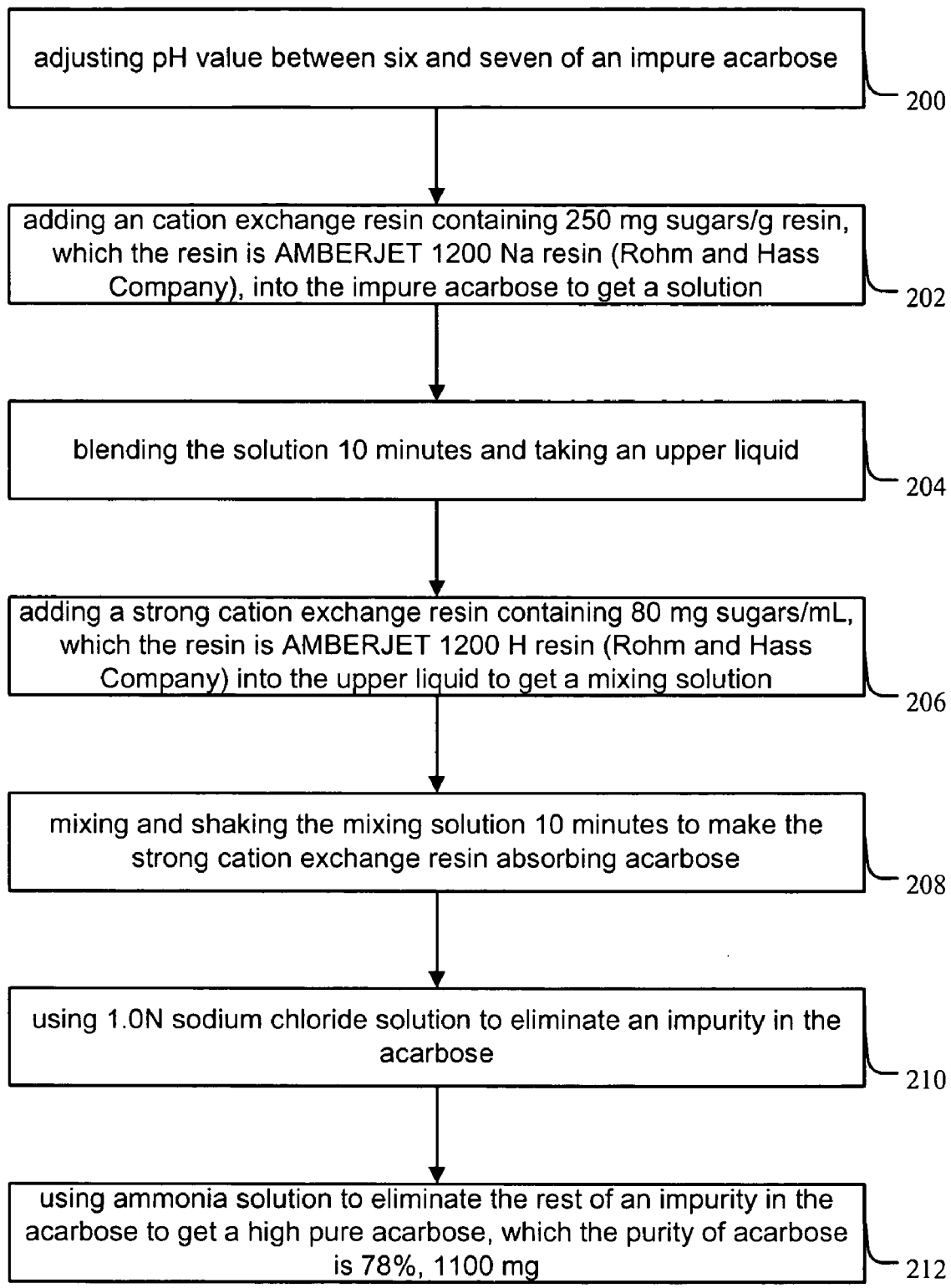
FIG. 3 is flow chart showing a purification process for manufacturing a highly pure acarbose of Example 2 of the present invention.

Referring to FIG. 3, the present invention comprises the following steps:

Step 200: adjusting the pH value of an impure acarbose to between six and seven;

Step 202: adding a cation exchange resin containing 250 mg sugar/g into the impure acarbose, in which the resin is AMBERJET 1200 Na (Rohm and Hass Company), in order to obtain a solution;

Step 204: blending the solution for 10 minutes and taking the upper liquid;

Step 206: adding a strong cation exchange resin containing 80 mg sugars/mL into the upper liquid, in which the resin is AMBERJET 1200 H resin (Rohm and Hass Company), to obtain a mixing solution;

Step 208: mixing and shaking the mixing solution for 10 minutes to make the strong cation exchange resin absorb acarbose;

Step 210: using a 1.0N sodium chloride solution to eliminate an impurity in the acarbose; and Step 212: using an ammonia solution to eliminate further impurities in the acarbose to obtain a highly pure acarbose having a purity of 78%, 1100 mg.

EXAMPLE 3

Figure 4:
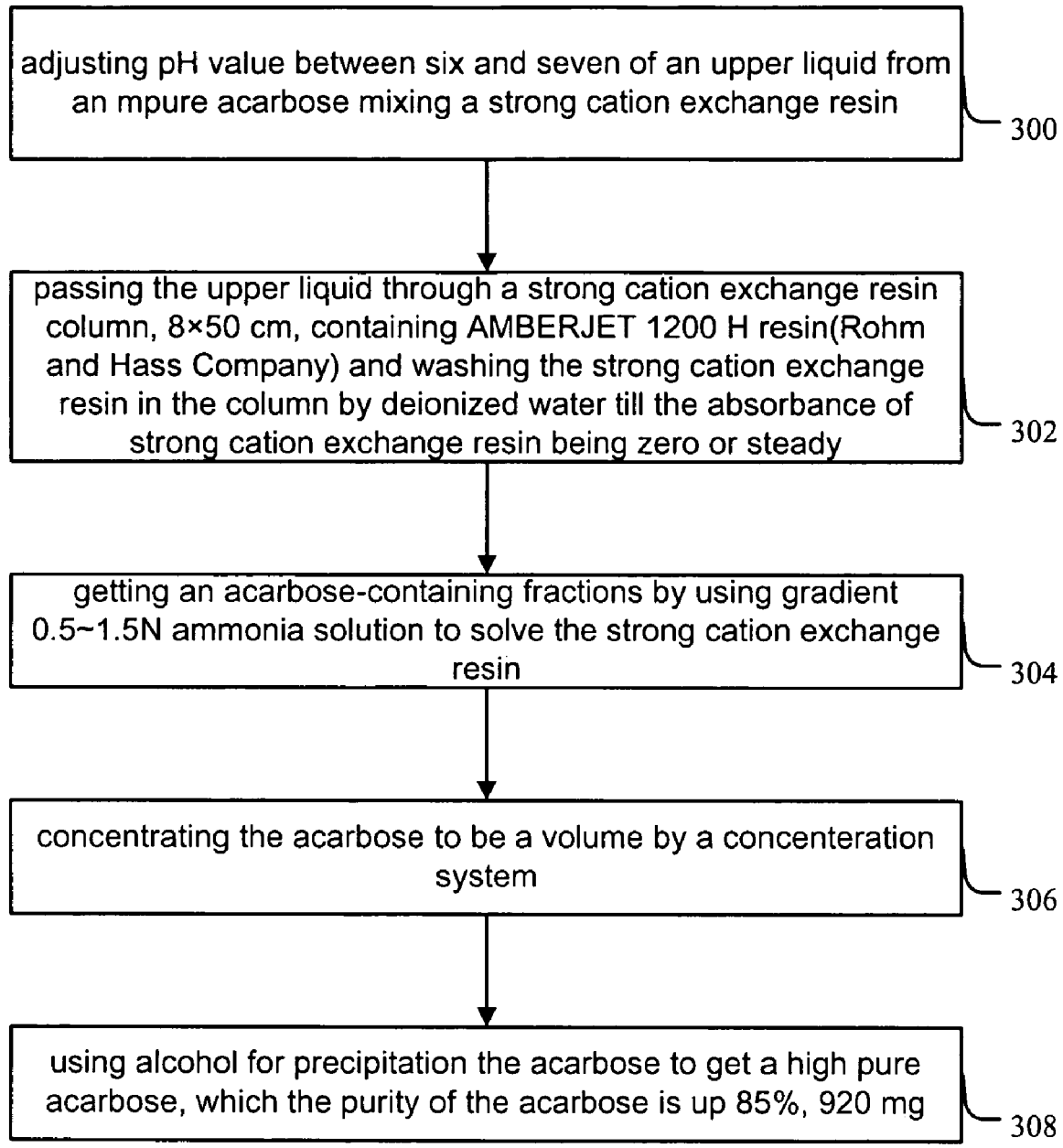
FIG. 4 is flow chart showing a purification process for manufacturing a highly pure acarbose of Example 3 of the present invention.

Referring to FIG. 4, the present invention comprises the following steps:

Step 300: adjusting the pH value of an upper liquid from an impure acarbose mixed with a strong cation exchange resin to between six and seven;

Step 302: passing the upper liquid through a strong cation exchange resin column, 8×50 cm, containing AMBERJET 1200 H resin (Rohm and Hass Company) and washing the strong cation exchange resin in the column with deionized water until the absorbance of the strong cation exchange resin is zero or steady;

Step 304: getting acarbose-containing fragments by using a gradiated 0.5~1.5N ammonia solution to dissolve the strong cation exchange resin;

Step 306: concentrating the acarbose to a certain volume by a concentrating system; and Step 308: using alcohol to precipitate the acarbose to obtain a highly pure acarbose, in which the purity of the acarbose is up 85%, 920 mg.

EXAMPLE 4

Figure 5:
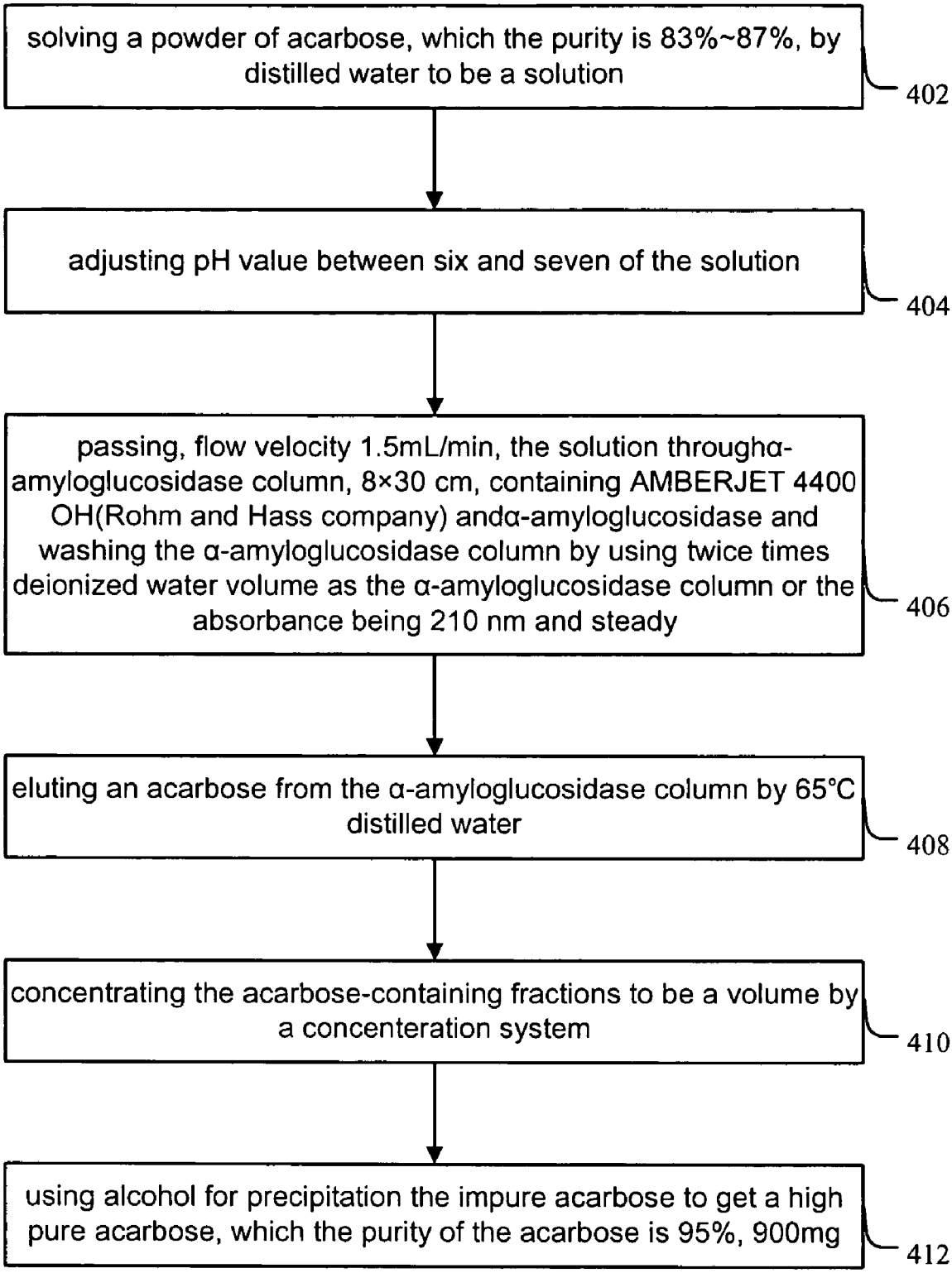
FIG. 5 is flow chart showing a purification process for manufacturing a highly pure acarbose of Example 4 of the present invention.

Referring to FIG. 5, the purity of the acarbose powder of the present invention is 85% as discussed in Example 3 and using this example, the present invention comprises the steps of:

Step 402: dissolving a powder of acarbose having a purity of 83%~87%, using distilled water, to create a solution;

Step 404: adjusting the pH value of the solution to between six and seven;

Step 406: passing, with a flow velocity of 1.5mL/mn, the solution through an α-amyloglucosidase column, 8×30 cm, containing AMBERJET 4400 OH (Rohm and Hass company) and α-amyloglucosidase, and washing the α-amylglucosidase column by using a volume of deionized water twice that of the α-amyloglucosidase column or the absorbance being 210 nm and steady;

Step 408: eluting an acarbose from the α-amyloglucosidase column using 65° C. distilled water;

Step 410: concentrating the acarbose-containing fragments to be a volume by a concentrating system; and Step 412: using alcohol to precipitate the impure acarbose to get a highly pure acarbose having a purity of 95%, 900 mg.

ADVANTAGES OF THE INVENTION

The above four examples can achieve highly pure acarbose appropriate for use as a medical drug, simplify the processes and decrease product costs by using low-cost resin.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A purification process for manufacturing a highly pure acarbose from an acarbose-containing fermentation broth, comprising the steps of:

using alcohol for precipitation of a concentrate from the fermentation broth;

mixing alcohol with the concentrate to form a sediment;

dissolving the sediment using distilled water to form an impure acarbose solution;

using a strong cation exchange chromatography and an immobilized enzyme affinity chromatography for purification of the impure acarbose solution.

2. The purification process of claim 1, wherein the strong cation exchange chromatography uses a styrene divinylbenzene copolymer without methoxymethylmethacrylamide as a resin matrix.

3. The purification process of claim 1, wherein the immobilized enzyme affinity chromatography has an enzyme which uses α-amylogluosidase(α-glucoamylase).

4. The purification process of claim 1, wherein the strong cation exchange chromatography uses a cation exchange resin containing 20-200 mg sugars/mL.

5. The purification process of claim 2, wherein, after strong cation exchange chromatography, a 0~2N ammonia solution is used as a solvent to manufacture highly pure acarbose.

6. The purification process as claim 3, wherein, after the immobilized enzyme affinity chromatography, 55~75° C. distilled water is used as a solvent to manufacture a highly pure acarbose.

7. The purification process of claim 1, wherein the purity of highly pure acarbose is larger than 95% (wt/wt) and suitable for use in treating diabetes.

8. A purification process for manufacturing a highly pure acarbose, comprising the steps of:

dissolving an acarbose powder having a purity of 83%-87% with distilled water, to form a solution;

adjusting the pH value of the solution;

passing the solution through an α-amyloglucosidase column;

washing the α-amyloglucosidase column by using a volume of deionized water equal to twice the volume of the α-amyloglucosidase column;

eluting acarbose fragments from the α-amyloglucosidase column using distilled water;

concentrating the acarbose-containing fragments to a volume of impure acarbose using a concentrating system; and precipitating the impure acarbose to obtain a highly pure acarbose.

9. The purification process of claim 8, wherein the flow velocity passing through the α-amyloglucosidase column is 1.5 mL/min.

10. The purification process of claim 9, wherein the step of washing the α-amyloglucosidase column uses a volume of deionized water equal to twice the volume of the α-amyloglucosidase column.

11. The purification process of claim 9, wherein washing the α-amyloglucosidase column with deionized water changes the flow velocity passing through the α-amyloglucosidase column to 210 nn until the absorbance of the α-amyloglucosidase is steady.

12. The purification process of claim 9, wherein the step of dissolving the acarbose powder from the α-amyloglucosidase column uses 65° C. distilled water.

13. The purification process of claim 9, wherein the purity of the highly pure acarbose is up to 95%.

\* \* \* \* \*

UNITED STATES PATENT AND TRADEMARK OFFICE
CERTIFICATE OF CORRECTION

| | |
|---|---|
| PATENT NO. | : 7,253,278 B2 |
| APPLICATION NO. | : 10/790069 |
| DATED | : August 7, 2007 |
| INVENTOR(S) | : Chung-Liang Lin et al. |

Page 1 of 1

It is certified that error appears in the above-identified patent and that said Letters Patent is hereby corrected as shown below:

Title Page in section [73] Assignee, change "Chinese Petroleum Corporation, Taipei, Taiwan, R.O.C." to --CPC Corporation, Taiwan, Taipei, Taiwan, R.O.C.--

Signed and Sealed this

Nineteenth Day of February, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,253,278 B2 |
| APPLICATION NO. | : 10/790069 |
| DATED | : August 7, 2007 |
| INVENTOR(S) | : Chung-Liang Lin et al. |

Page 1 of 1

It is certified that error appears in the above-identified patent and that said Letters Patent is hereby corrected as shown below:

On title page in Item [73] Assignee, change "Chinese Petroleum Corp., Taipei (TW)" to --CPC Corporation, Taiwan, Taipei (TW)--.

Signed and Sealed this

Eighteenth Day of March, 2008

JON W. DUDAS
*Director of the United States Patent and Trademark Office*